US00PP17070P2

(12) United States Plant Patent
Oud

(10) Patent No.: US PP17,070 P2
(45) Date of Patent: Aug. 29, 2006

(54) ***OSTEOSPERMUM* PLANT NAMED 'OSJAMWHIT'**

(50) Latin Name: *Osteospermum ecklonis*
Varietal Denomination: Osjamwhit

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 10 days.

(21) Appl. No.: 11/167,496

(22) Filed: Jun. 27, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
*Assistant Examiner*—June Hwu
(74) *Attorney, Agent, or Firm*—Bruce Vrana

(57) ABSTRACT

A new *Osteospermum* plant particularly distinguished by its very compact round plant habit, early flowering with white colored ray florets and blue colored disc florets.

1 Drawing Sheet

Latin name of the genus and species of the plant claimed: *Osteospermum ecklonis*.

Varietal denomination: 'Osjamwhit'.

BACKGROUND OF THE NEW PLANT

The present invention relates to a new and distinct cultivar of *Osteospermum* plant, botantially known as *Osteospermum ecklonis*. The new *Osteospermum* is propagated by cuttings resulting from a cross of a proprietary *Osteospermum ecklonis* seedling selection as the male, or pollen, parent identified as code number 'C272' with a proprietary *Osteospermum ecklonis* selection identified as code number 'C298' as the female, or seed, parent. 'C272' has a plant height of 30 cm and a plant width of 20 cm. 'C298' has a plant height of 18 cm and a plant width of 12 cm.

The new *Osteospermum* was discovered and selected as a single flowering plant within the progeny of the stated cross grown in Enkhuizen, Netherlands in 1998. Neither 'C272' nor 'C298' has been patented. The new *Osteospermum* plant has been repeatably asexually reproduced by cuttings in Enkhuizen, Netherlands over a period of four years. It has been found to retain its distinctive characteristics through successive propagations, and this novelty appears to be firmly fixed.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Osteospermum* plant. The data which defines these characteristics were collected from asexual reproductions carried out in Enkhuizen, Netherlands. The plant history was taken on 15 weeks old plants. Color references are primarily to The R.H.S. Colour Chart of The Royal Horticultural Society of London. The instant plant was grown indoors in a 10.5 cm container.

TABLE 1

Comparison between the new cultivar 'Osjamwhit' and a similar cultivar

| | 'Osjamwhit' | 'Bright side' (Unpatented) |
|---|---|---|
| Plant height | 28 cm | 30 cm |
| Plant width | 18 cm | 20 cm |
| Flowering response | | Opening of first flower one week later |

The plant:

*Classification.*—Botanical *Osteospermum ecklonis*.

Parentage:

*Female parent.*—A seedling named 'C298' is one of our seedlings from our C-generation of plants bred in 1998.

*Male parent.*—A seeding named 'C272' is one of our seedlings from one C-generation of plants bred in 1998.

Plant description:

*Growth habit.*—Round, compact.

*Plant height.*—28 cm.

*Speading area of plant.*—18 cm.

*Strength.*—Moderate growth.

*Branching character.*—Freely branching, 20 lateral branches without pinching.

*Blooming period.*—From May until October.

The stem:

*Length.*—9 cm.

*Diameter.*—4 mm.

*Intermode length.*—8 mm.

*Texture.*—Glabrous.

*Color.*—RHS 137C.

The foliage:

*Shape.*—Single leaves, alternate and elliptic, apex: broadly acute base: attenuate, margin: irregular serration.

*Number of leaves per lateral branch.*—14.

*Texture.*—Glabrous, leathery.

*Leaf.*—Color — Upper side: RHS 137A. Color — Under side: RHS 137B. Length: Young 30 mm, mature 70 mm. Width: Young 10 mm, mature 45 mm.

*Petiole.*—Absent.

The inflorescence:

*Number of inflorescences per mature plant.*—90.

*Inflorescence bud.*—Form: Ovoid. Length: 24 mm. Width: 10 mm. Color: RHS 94C.

*Inflorescence lastingness on the plant.*—Around 5 days depending on the temperature.

*Inflorescence.—Diameter:* 65 mm. Disc diameter: 9 mm.

*Disc florets.*—Shape: Tubular, elongated. Apex: Five pointed. Length: 7 mm. Width: 1 mm. Number of disc florets per inflorescence: 40. Color: RHS 96C.

*Inflorescence depth.*—12 mm.

*Fragrance.*—No fragrance.

*Ray florets.*—Length: 28 mm. Width: 9 mm.

*Shape.*—Capitulum with one series of ray florets. Color. Upper surface: RHS N155A. Lower surface: RHS 94C. At base: RHS 77A. Number of ray florets: 18. Shape — Apex: Rounded. Base: Acute. Margin: Entire. Texture: Satiny.

*Peduncles.*—Length: 6 cm. Texture: Sturdy, tiny hairs. Color: RHS 137C. Diameter: 1.5 mm. Shape: Round.

*Phyllaries.*—Texture: Rough, tiny hairs. Number of phyllaries: 18. Color: RHS 137C. Length: 8 mm. Margin: Entire. Width: 1.5 mm. Apex: Acute. Shape: Ligulate. Color: RHS 137C both sides.

Reproductive organs:

*Androecium.*—Appearance: Present on disc florets only. Shape: Oblong, five stamen fused to one. Length: 2 mm. Width: 1 mm. Pollen color: RHS 25A. Total no. of anthers: 40.

*Gynoecium.*—Appearance: Present on both ray and disc florets. Pistil number: One pistil per ray or disc floret. Pistil length: 3 mm. Stigma color: RHS 83A. Stigma shape: Bipartite.

Seed development: Seed development has been observed on plants of the new *Osteospermum.*

*Amount of seeds produced.*—Moderate.

*Seed length.*—5 mm.

*Diameter.*—2 mm.

*Color.*—RHS 199A.

*Shape.*—Elliptic.

Disease resistance: Under commercial conditions, plants of the new *Osteospermum* are resistant to fungal pathogens common to *Osteospermum.*

What is claimed is:

1. A new and distinct variety of *Osteospermum* plant, substantially as illustrated and described herein.

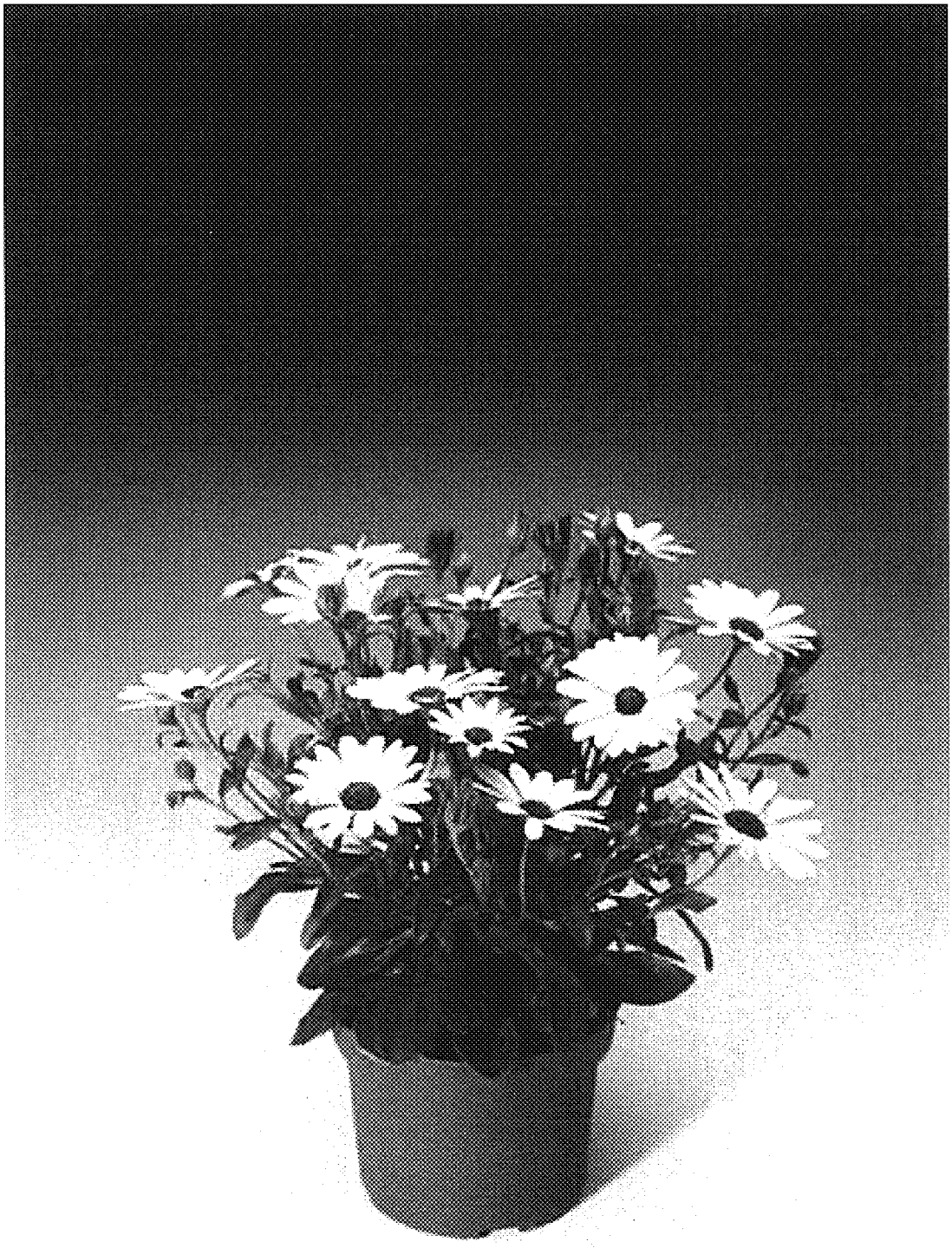

* * * * *